United States Patent [19]

Sneider

[11] 4,225,062
[45] Sep. 30, 1980

[54] EXPANDING SYRINGE WITH FILLING VALVE

[76] Inventor: Vincent R. Sneider, 3422 Hallcrest Dr, Atlanta, Ga. 30319

[21] Appl. No.: 967,463

[22] Filed: Dec. 7, 1978

[51] Int. Cl.$^2$ .............................................. A61M 3/00
[52] U.S. Cl. ................................. 222/211; 128/251; 222/508; 222/567
[58] Field of Search .................. 128/251, 232, 239; 141/351, 352; 222/81, 83, 89, 107, 211, 215, 567, 505, 508, 517, 400.7

[56] References Cited

U.S. PATENT DOCUMENTS

| | | | |
|---|---|---|---|
| 2,969,168 | 1/1961 | Newby | |
| 3,104,032 | 9/1963 | Hansen | 128/232 UX |
| 3,141,580 | 7/1964 | Rodgers | |
| 3,321,114 | 5/1967 | Croyle | |
| 3,401,695 | 9/1968 | Rosenberg et al. | 222/107 X |
| 3,754,553 | 8/1973 | Hewitt et al. | 128/251 X |
| 3,823,848 | 7/1974 | Schuster et al. | 222/400.7 X |
| 3,986,509 | 10/1976 | Sneider | 128/251 |
| 3,993,070 | 11/1976 | Sneider | 128/251 |

Primary Examiner—David A. Scherbel
Attorney, Agent, or Firm—Robert L. Niblack; Neil E. Hamilton

[57] ABSTRACT

A feminine syringe unit wherein a housing with a valve member and nozzle serve as both a filling and dispensing port for an expandable syringe bag. The syringe unit includes a removable nozzle retainer which has slidably secured thereto a nozzle member. When the nozzle member is removed, the bag is easily filled through a filling orifice and a dispensing flap valve. For cleaning and drying purposes, the valve is also removable from the bag by means of its being engaged by a valve retainer which in turn is threadably engaged on a bag retainer. The unit is activated by moving the nozzle toward the bag whereby the inlet portion of the nozzle will abut against a flap valve so as to create fluid communication between the inside of the bag and the nozzle. A hold-open means is also provided for the nozzle inlet portion in the valve member so that when a force is exerted on the bag to eject liquid through the nozzle it will not force the valve closed.

18 Claims, 5 Drawing Figures

U.S. Patent  Sep. 30, 1980  Sheet 1 of 3  4,225,062
FIG. 2
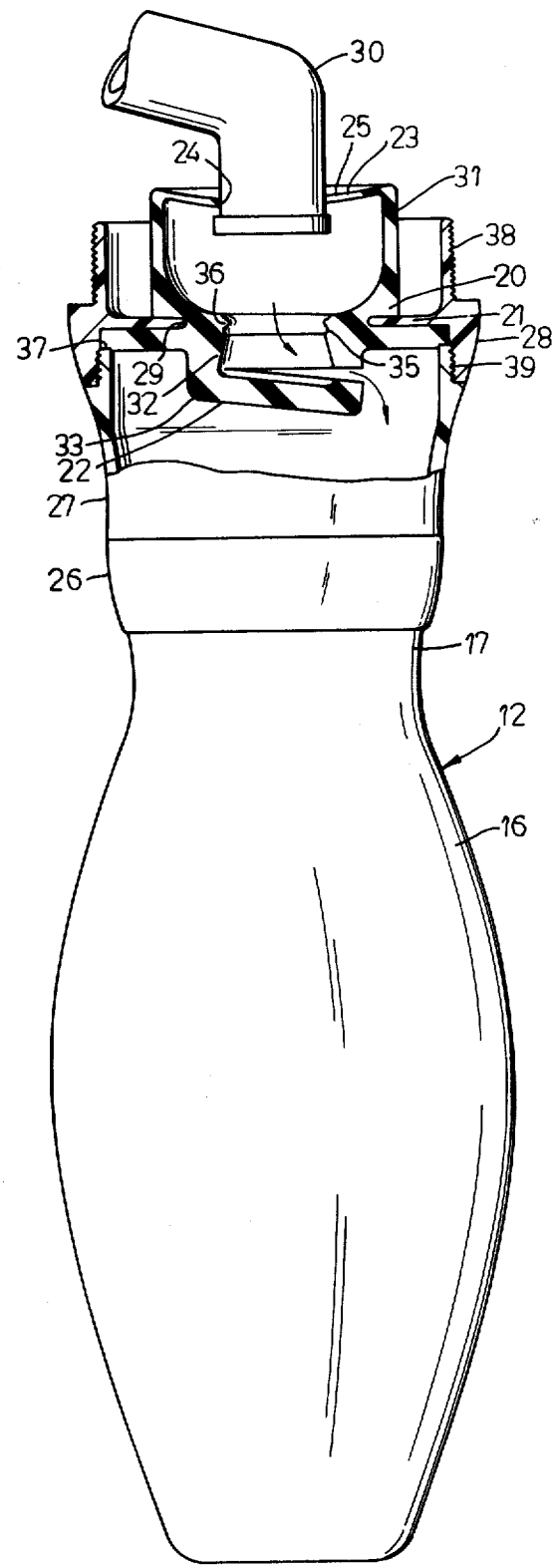
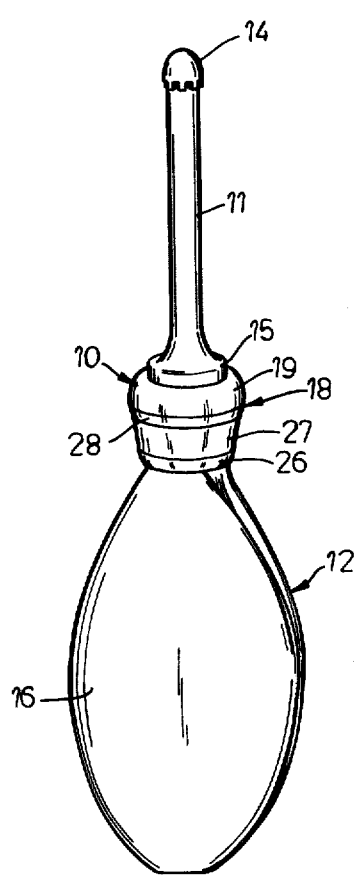
FIG. 1

EXPANDING SYRINGE WITH FILLING VALVE

BACKGROUND OF THE INVENTION

This invention relates to a syringe unit which utilizes an expandable bag and to a unique filling and dispensing system which will permit filling of the bag as well as dispensing of its contents. More particularly, this invention is concerned with a filling and dispensing means for an expandable syringe unit which can be easily disassembled so as to afford a filling of the bag as well as cleaning and drying thereof.

Syringe units of the type concerned with in this invention are described in U.S. Pat. Nos. 2,969,168; 3,141,580; 3,321,114; 3,986,509 and 3,993,070. In U.S. Pat. No. 2,969,168 a dispensing type closure is described for a fluid containing receptacle and the same is true regarding U.S. Pat. No. 3,141,580. In U.S. Pat. No. 3,321,114 a buckle-type hinge for a container closure is illustrated and in U.S. Pat. No. 3,986,509 a sliding-type extending valve arrangement is shown with a douche syringe. A flap valve arrangement is disclosed in U.S. Pat. No. 3,993,070 for purposes for filling an expandable syringe.

The prior art does not disclose a valving arrangement for an expandable syringe which can serve to receive both a filling orifice such as the head of a faucet and also receive and be actuated by the inlet portion of a dispensing nozzle. Neither is the prior art concerned with an expandable syringe which can be disassembled so as to permit the bag to be cleaned and dried and readily reassembled so as to afford filling and ultimately dispensing of the bag contents.

It is an advantage of the present invention to provide a combined filling and dispensing port for an expandable syringe. Other advantages are a dispensing valve arrangement for an expandable syringe which is actuated by a nozzle member and the valve is held in a positive open position during dispensing; an expandable syringe unit which can be disassembled to permit cleaning and drying of the bag as well as access to the filling orifice for filling purposes; a closure for an expandable douche bag which will afford a fluid-tight engagement with a nozzle and have an esthetic appearance; and an expandable syringe unit which is reusable and is easily operated.

SUMMARY OF THE INVENTION

The foregoing advantages are accomplished and the shortcomings of the prior art are overcome by the combined filling and dispensing port for an expandable syringe which includes a hollow nozzle defining a hollow spray stem with an inlet portion, a head and a holder portion. An expandable bag has a neck portion to receive a closure housing defined by a nozzle retaining portion providing a limited slide path for the nozzle holder. A valve member is provided in the closure housing which has a nozzle actuated portion and a filling portion with an orifice. The inlet portion of the nozzle is constructed and arranged in conjunction with the nozzle holder portion and the nozzle retaining portion guide path to be positioned through the filling orifice and to contact the nozzle actuated portion. Means are provided to secure the bag to the housing as well as to detachably remove the nozzle retainer and the nozzle member from the bag and the closure housing. In a preferred manner, the nozzle actuated portion of the valve is provided by means of a flap valve which is contacted by the inlet portion of the nozzle when the nozzle is moved toward the inside of the bag. A sealing portion is provided in the throat of the nozzle actuated portion of the valve member to contact the nozzle inlet portion and in conjunction therewith, a hold-open means is also provided by a projecting flange on the nozzle inlet portion and an accommodating groove in the valve member. Also in a preferred manner, the filling portion of the valve member is formed from a thin diaphragm portion defining an orifice.

The expandable syringe unit is constructed and arranged so that the expandable bag with a bag retainer element provides one component; a valve member defining a nozzle actuated portion and a filling portion having an orifice, the valve element including a valve retainer portion forms another component; and a nozzle retainer with a hollow nozzle having a spray stem with an inlet portion, a head and a holder portion provides a third component. These components are threadably fitted together so that the valve retainer portion is secured to the bag retainer element and the nozzle retainer is engaged on the valve retainer. In this manner, the nozzle can be removed from the valve so as to afford access to the filling portion for filling purposes and subsequently, both the nozzle member and the valve member can be removed to provide complete access to the bag for drying and cleaning.

BRIEF DESCRIPTION OF THE DRAWINGS

A better understanding of the present combined filling and dispensing port for an expandable syringe will be accomplished by reference to the drawings wherein:

FIG. 1 is a side perspective view showing the assembled syringe unit prior to filling.

FIG. 2 is an enlarged view and partially in vertical section showing the nozzle removed and the unit engaged by a faucet head for filling.

DESCRIPTION OF THE PREFERRED EMBODIMENT

Figure 3:
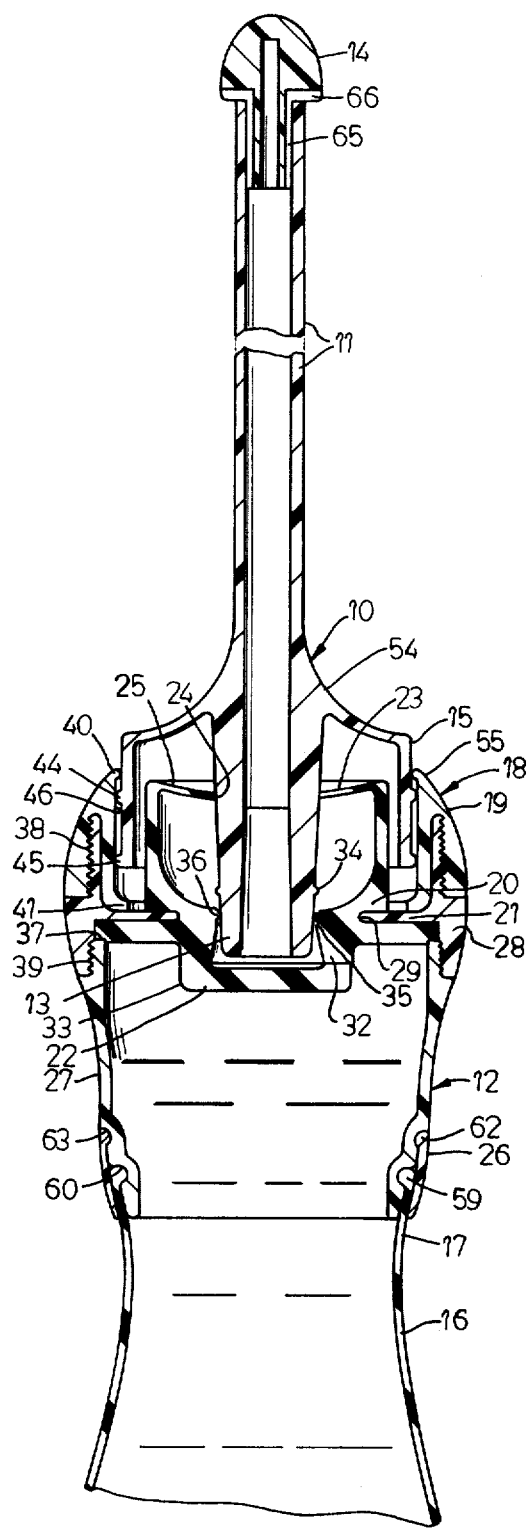
FIG. 3 is an enlarged view in vertical section illustrating the syringe unit after filling and prior to activation.

Proceeding to a detailed description of a preferred embodiment of the present invention, the combined filling and dispensing port 10 is shown in conjunction with an expandable syringe unit 12 having the usual hollow nozzle or spray stem 11 of the feminine type and an expandable bag 16. A closure housing 18 includes a nozzle retainer 19 as well as a valve retainer 28 and a bag retainer 27. A bag holding ring 26 provides the means for attaching bag 16 to housing 18.

Referring specifically to FIG. 2, it will be seen that a valve member 20 is secured in housing 18 by means of a valve retainer 28 threadably engaged on bag retainer 27 by means of threads 39. Valve retainer 28 has an inwardly extending annulus 21 which is receivable in an annular groove 29 in the valve member 20. The threaded engagement 39 will cause valve member 20 to seat against the threaded section such as shown at 37 for a fluid-tight engagement. Valve member 20 has a filling portion 23 formed by a diaphragm 25 in which is disposed a filling orifice 24 to receive the faucet head 30. At the opposite end of the valve and at the base of annular wall 31 is a throat section 32 which includes a sealing portion 36 and a flap valve portion 22 which is attached to valve member 20 by hinge section 33.

Figure 4:
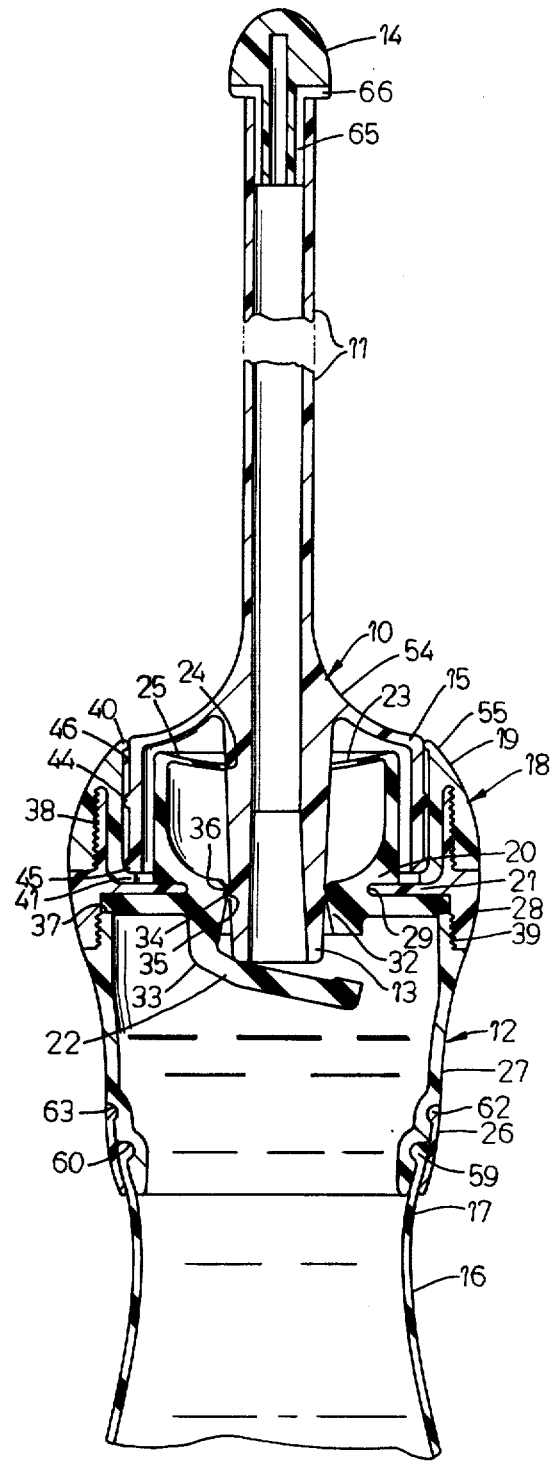
FIG. 4 is a view similar to FIG. 3 showing the syringe unit in the activated position.

As best seen in FIGS. 3 and 4, housing 18 also includes a nozzle retainer 19 slidably attached to nozzle holder portion 15 forming a part of nozzle 11. Nozzle retainer 19 is threadably disposed on valve retainer 28 by means of threads 38. Nozzle retainer 19 includes two internal flanges 40 and 41 as well as an annular wall surface 46 disposed therebetween. External flanges 44 and 45 are spaced apart on nozzle holder portion 15 and are positioned so as to ride over wall surface 46 yet are in an interference fitment with internal flanges 40 and 41 so as to slidably but captively hold the nozzle 11 on the nozzle retainer 19. It will be seen that the nozzle inlet portion 13 has a projecting flange 34 which is accommodated in a groove 35 when the nozzle is moved to a position as shown in FIG. 4 and the nozzle inlet portion is in contact with the flap valve portion 22 so as to cause it to open. The placement of flange 34 in groove 35 provides a hold-open means for the flap valve 22. It will be noted that flange 34 is of such a size so that it can ride through the sealing portion 36 and the throat section 32 of valve member 20 with groove 35 placed in close proximity to the sealing portion. Bag 16 with neck portion 17 is secured to housing 18 and specifically to bag retainer 27 by means of bag bead 59 seated in groove 60 and held therein by means of bag holding ring 26 having a bead 62 for frictional seating in groove 63 of bag retainer 27.

Nozzle head 14 is of a lateral spray type and is the subject matter of U.S. patent application Ser. No. 774,046 filed Nov. 22, 1976 by the same inventor and entitled "Expandable Syringe and Means for Storing Chemical Agents for Use Therewith". It provides longitudinal channels 65 between head 14 and the hollow nozzle 11 which channels communicate with radial passages 66.

Figure 5:
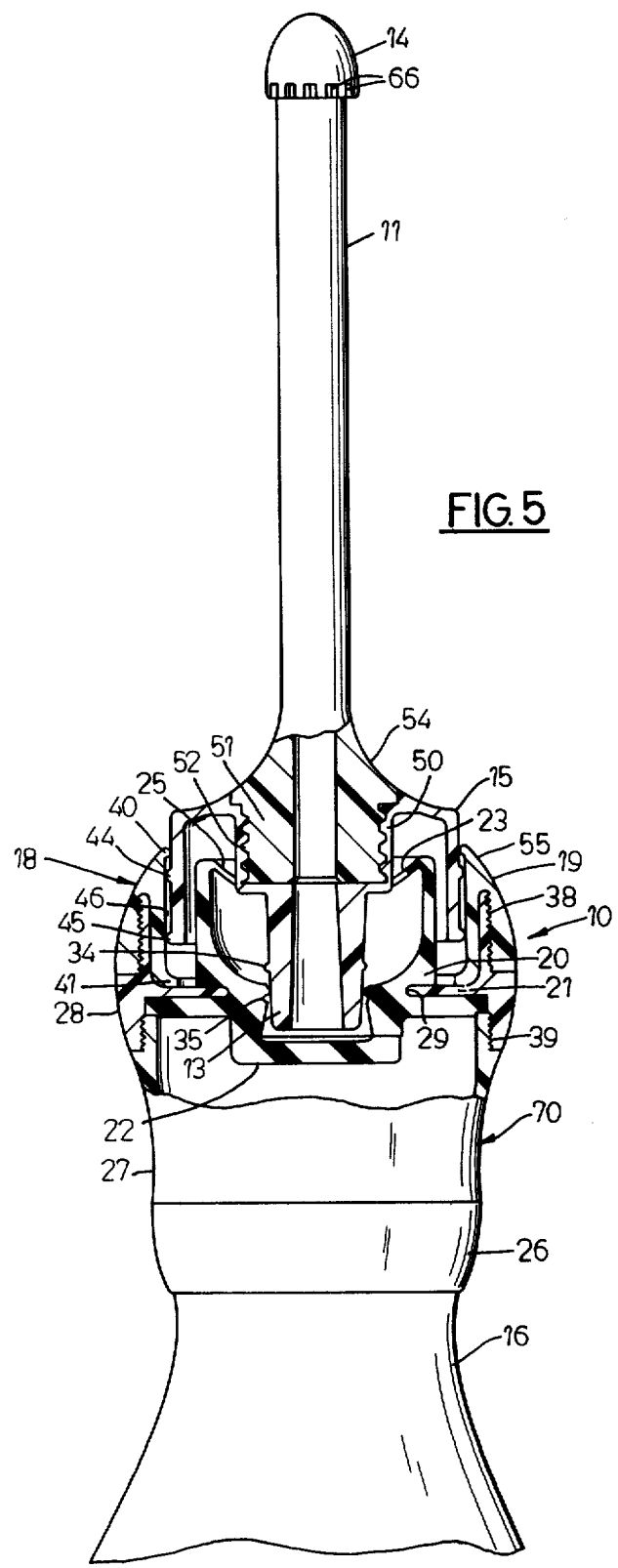
FIG. 5 is a view similar to FIG. 3 showing an alternative embodiment.

Referring to FIG. 5, an alternative embodiment is shown therein. This syringe unit 70 utilizes basically the same components as a syringe unit 10 except that the nozzle member 11 and the nozzle holder 15 are not formed as one unit. Instead, nozzle 11 has a connecting section 51 with threads 52 for threadable engagement with annular compartment 50 which is a part of nozzle holder portion 15.

OPERATION

A better understanding of the advantages of the filling and dispensing port 10 and syringe unit 12 will be had by a description of their operation. The syringe unit 12 will be packaged as shown in FIG. 1 with the nozzle 11 secured to bag 16 by means of closure housing 18. When it is desired to fill bag 16 with liquid, preferably in the form of water, nozzle retainer 19 will be unscrewed from valve retainer 28 so as to remove the nozzle and expose the filling portion 23 of valve member 20. Faucet head 30 will then be inserted through filling orifice 24 and diaphragm 25 will be of sufficient strength so as to prevent any splashing of the water out from the valve body. The force of the water entering the valve body will be sufficient to force flap valve 22 open permitting the water to flow into bag 16. This is best seen in FIG. 2. As the liquid fills the bag 16 it will be appreciated that the construction of bag 16 is such that the walls will expand thus creating an expansive force on the contents of the bag. When the flow of liquid from the faucet ceases, the force of the liquid in the bag will cause flap valve 22 to close. Faucet head 30 will then be withdrawn from filling portion 23 and nozzle 11 by means of nozzle retainer 19 will be screwed back onto valve retainer 28. The syringe unit 12 will now be in the condition shown in FIG. 3. When it is desired to activate the syringe unit, a force will be exerted on nozzle 11, and preferably on the exterior wall portion 54 of nozzle holder portion 15, and the nozzle moved toward the inside of bag 16. This motion will cause the nozzle inlet portion 13 to contact flap valve 22 and at the same time projecting flange 34 to ride over and through sealing portion 36 of throat section 32 in valve member 20. This movement will continue until projecting flange 34 will seat itself in groove 35. At this point, the flap valve 22 will assume a position shown in FIG. 4. With flap valve 22 in the open position, liquid under the pressure of bag 16 will automatically flow around the flap valve into the inlet portion 13 of nozzle 11, through nozzle 11, along channels 65 and ultimately outwardly by means of radial ports 66. The nozzle will be held in the open position by means of the hold-open means effected by projecting flange 34 seating itself in groove 35. When it is desired to deactivate the syringe all that is required is an outward pulling on nozzle 11 which will then cause projecting flange 34 to unseat itself from groove 35 and flap valve 22 to assume a closed position as the nozzle inlet portion 13 moves to a position shown in FIG. 3.

During the previously described opening and closing of flap valve 22 it will be appreciated that nozzle holder portion 15 with external flanges 44 and 45 will have moved over wall surface 46 of nozzle retainer 19. This wall surface 46 provides a guide surface for flanges 44 and 45. It will further be seen that movement of nozzle holder portion 15 and consequently nozzle 11 is limited by means of internal flanges 40 and 41 extending from nozzle retainer 19. Accordingly, limited inward and outward movement of the nozzle is effected by means of the previously described flanges to effect a limited travel stop means.

When it is desired to either completely empty the contents of bag 16 or to clean or dry it, complete access to the bag is afforded by unscrewing valve retainer 28 from bag retainer 27. This will remove the valve member 20, as well as nozzle retainer 19 if present, so that the bag 16 can be inverted and folded through bag retainer 27 for drying purposes.

The syringe unit 70 shown in FIG. 5 will operate in the same manner as previously described for unit 12. The only difference will be in the manner in which the nozzle 11 is attached to nozzle holder portion 15. This is effected merely by screwing the connecting section 51 with threads 52 into the annular compartment 50 of nozzle holder portion 15. The syringe unit 70 will then operate as previously described for unit 12.

It should be further noted that actuation of syringe units 12 and 70 is conveniently effected by having the external wall portion 54 of nozzle holder portion 15 extend outward from the external wall portion 55 of nozzle retainer 19. This affords an easy gripping section for movement of the nozzle inwardly into housing 18. It should also be pointed out that when the nozzle is in an operative position such as shown in FIG. 4, the wall portions 54 and 55 will be coextensive thus preventing any foreign matter entering between the nozzle holder 15 and housing 18. This is effected by contact of flanges 41 and 45 of nozzle retainer 19 and nozzle holder 15, respectively, and forming part of the limited travel stop means.

As previously described, valve member 20 and valve retainer 28 are formed from two components. If desired, they could be formed as one although it is preferable to have the valve member 20 formed from a rubber or Kraton material and valve retainer 28 as well as nozzle 11, nozzle holder portion 15, nozzle retainer 19, and bag retainer 27 as well as bag holding ring 26 formed from a rigid plastic material such as high density polyethylene. However, other materials such as styrene could be employed. While a particular head 14 is described for use with nozzle 11, it will be appreciated that any effective spray head could be employed and attached to nozzle 11 as a separate part or molded integrally therewith.

It will thus be seen that through the present invention there is now provided a combined filling and dispensing port for an expandable syringe which allows complete disassembly of the dispensing port for access to the bag as well as partial disassembly to permit a filling operation. The syringe unit is actuated in a simple manner in that the contents of the bag are under pressure yet the valve mechanism is held in a positive open position by means of a unique interfitment between the nozzle member and the valve member. An esthetically pleasing and smooth design configuration is provided for the closure housing in that the various components are in axial alignment by means of the alignment of the various thread connections and also the mating of wall sections 54 and 55 of nozzle holder portion 15 and nozzle retainer 19 when the unit is in an activated position.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. A combined filling and dispensing port for an expandable syringe unit comprising:
    a hollow nozzle defining a hollow spray stem with an inlet portion, a head and a holder portion;
    an expandable bag having a neck portion;
    a housing defined by a detachable nozzle retainer portion providing a limited slide path for said nozzle holder portion;
    a valve member defining a nozzle actuated portion and a filling portion having an orifice carried in said housing;
    means to secure said neck portion of said bag to said housing;
    said inlet portion of said nozzle constructed and arranged in conjunction with said holder portion and said nozzle retainer portion slide path to be positioned through said filling orifice and to contact said nozzle actuated portion;
    whereby said nozzle retainer portion with said nozzle member can be detached from said valve member and a filling pipe or faucet head can be inserted into said filling orifice to fill said bag with a liquid and subsequently said nozzle retainer portion with said nozzle can be operatively positioned through said filling orifice and in contact with said nozzle actuated portion so movement of said nozzle holder portion over said slide path of said nozzle holder and in the direction of said bag will open said nozzle actuated portion and provide fluid communication with the liquid in said bag.

2. The combined filling and dispensing port as defined in claim 1 wherein said nozzle actuated portion of said valve member is defined by a flap valve.

3. The combined filling and dispensing port as defined in claim 2 wherein said nozzle actuated portion of said valve member further includes a throat section and said inlet portion of said nozzle and said throat section define a tentative hold-open means for said flap valve when said nozzle contacts said flap valve in the hold-open position.

4. The combined filling and dispensing port as defined in claim 3 wherein said hold-open means is defined by a projecting flange extending from said nozzle inlet portion and an accommodating groove in said valve member.

5. The combined filling and dispensing port as defined in claim 2 wherein said nozzle actuated portion of said valve member includes a sealing portion for slidable engagement with the inlet portion of said nozzle.

6. The combined filling and dispensing port as defined in claim 5 further including a projecting flange extending from said nozzle inlet portion, said flange constructed and arranged to ride through said sealing portion and an accommodating groove positioned in close proximity to said sealing portion and in the direction of said flap valve.

7. The combined filling and dispensing port as defined in claim 1 wherein said filling portion of said valve member comprises a thin diaphragm portion defining said orifice.

8. The combined filling and dispensing port as defined in claim 1 wherein said housing includes a valve retaining means secured to said valve member and said valve retaining means is attached to said nozzle retainer portion.

9. The combined filling and dispensing port as defined in claim 8 wherein said means to secure said neck portion of said bag includes a bag retainer portion secured to said valve retaining means.

10. The combined filling and dispensing port as defined in claim 9 wherein said valve retaining means is attached to said nozzle retainer portion and said bag retainer portion is secured to said valve retaining means by a threaded engagement.

11. The combined filling and dispensing port as defined in claim 1 wherein said nozzle retainer portion and said nozzle holder portion define a limited travel stop means to limit travel of said nozzle holder portion in said slide path of said nozzle retainer portion.

12. The combined filling and dispensing port as defined in claim 1 wherein said spray stem of said hollow nozzle and said nozzle holder portion are formed in two separate parts and secured together by threads.

13. The combined filling and dispensing port as defined in claim 11 wherein said limited travel stop means is constructed and arranged to position the exterior wall portions of said nozzle retainer portion and said nozzle holder portion in a coextensive manner when said nozzle inlet portion opens said nozzle actuated portion of said valve member.

14. An expandable syringe unit which can be disassembled into three basic components comprising:
    an expandable bag having a neck portion and a bag retainer element secured to said neck portion;
    a valve member defining a nozzle actuated portion and a filling portion having an orifice, said valve member including a valve retainer portion, said valve retainer portion detachably secured to said bag retainer element; and a nozzle retainer and a hollow nozzle defining a spray stem with an inlet portion, a head and a holder portion, said nozzle retainer providing a limited slide path for said nozzle holder portion and said nozzle retainer detachably secured to said valve retainer portion in a manner such that said inlet portion of said nozzle will contact said nozzle actuated portion of said valve member to provide fluid communication with the inside of said bag;

whereby said nozzle retainer with said nozzle can be removed from said valve retainer for purposes of filling said bag through said filling portion and said valve member can be removed from said bag retainer for purposes of drying the inside of said bag.

15. The expandable syringe unit as defined in claim 14 wherein said valve retainer portion is detachably secured to said bag retainer element and said nozzle retainer is detachably secured to said valve retainer portion by means of screw threads.

16. The expandable syringe unit as defined in claim 15 wherein said valve member and said valve retainer portion are formed as two separate components.

17. The expandable syringe unit as defined in claim 15 wherein said screw threads for attaching said valve retainer portion to said bag retainer element and said nozzle retainer to said valve retainer portion are in axial alignment.

18. The expandable syringe unit as defined in claim 14 wherein said nozzle is of the feminine type.

* * * * *